United States Patent
Kim

(10) Patent No.: US 10,195,032 B2
(45) Date of Patent: Feb. 5, 2019

(54) MITRAL CERCLAGE ANNULOPLASTY APPARATUS

(75) Inventor: June-Hong Kim, Busan (KR)

(73) Assignee: TAU PNU MEDICAL CO., LTD., Busan (KR)

( * ) Notice: Subject to any disclaimer, the term of this patent is extended or adjusted under 35 U.S.C. 154(b) by 0 days.

(21) Appl. No.: 13/252,217

(22) Filed: Oct. 4, 2011

(65) Prior Publication Data

US 2012/0029629 A1    Feb. 2, 2012

Related U.S. Application Data

(62) Division of application No. 12/631,803, filed on Dec. 4, 2009, now Pat. No. 8,231,671.

(Continued)

(30) Foreign Application Priority Data

Aug. 28, 2009    (KR) .......................... 10-2009-0080708

(51) Int. Cl.
 *A61F 2/24*    (2006.01)
 *A61B 17/04*    (2006.01)

(52) U.S. Cl.
 CPC .............. *A61F 2/246* (2013.01); *A61B 17/04* (2013.01); *A61B 17/0469* (2013.01); *A61F 2/2451* (2013.01); *A61F 2/2463* (2013.01); *A61B 2017/0496* (2013.01); *A61F 2/2466* (2013.01); *A61F 2250/0012* (2013.01)

(58) Field of Classification Search
 USPC ............... 623/2.36–2.37; 606/144, 148, 113; 289/17; 600/37
 See application file for complete search history.

(56) References Cited

U.S. PATENT DOCUMENTS

| | | | |
|---|---|---|---|
| 4,042,979 A | * | 8/1977 | Angell ........................ 623/2.37 |
| 5,536,273 A | | 7/1996 | Lehrer |

(Continued)

FOREIGN PATENT DOCUMENTS

| | | |
|---|---|---|
| KR | 10-2011-0023094 A | 8/2011 |
| KR | 10-1231140 B1 | 2/2013 |
| WO | 2012/043898 A1 | 4/2012 |

OTHER PUBLICATIONS

Kim, JH et al.; Mitral cerclage annuloplasty, a novel transcatheter treatment for secondary mitral valve regurgitation: initial results in swine; Translational Medicine Branch; Division of Intramural Research, National Heart Lung and Blood Institute, NIH, Bethesda, MD; Aug. 11, 2009; 29 Pages.

*Primary Examiner* — Leslie Lopez

(57) ABSTRACT

A mitral cerclage annuloplasty apparatus comprises a tissue protective device and a knot delivery device. The tissue protective device comprises a first protective tube and a second protective tube. The knot delivery device comprises a tube wherein a loose knot is looped around its distal end through a hole and wherein tight knot is formed when the distal end of the tube is cut open. Alternatively, the knot delivery device comprises an inner tube and outer tube. The inner tube is insertable and rotatable inside the outer tube. When the tubes are in a closed position by rotating either the outer tube or the inner tube, a hole is created near its distal end. When the tubes are in open position by rotating either the outer tube or the inner tube, the hole joins the opening of the outer tube and lengthens.

21 Claims, 6 Drawing Sheets

Related U.S. Application Data

(60) Provisional application No. 61/239,828, filed on Sep. 4, 2009.

(56) References Cited

U.S. PATENT DOCUMENTS

| | | | |
|---|---|---|---|
| 5,562,684 A | | 10/1996 | Kammerer |
| 6,161,547 A | * | 12/2000 | Barbut ............................ 128/898 |
| 6,217,610 B1 | * | 4/2001 | Carpentier et al. ........... 623/2.37 |
| 6,224,611 B1 | * | 5/2001 | Ouchi ............................ 606/113 |
| 6,402,781 B1 | * | 6/2002 | Langberg .............. A61F 2/2451 |
| | | | 623/1.11 |
| 6,790,229 B1 | * | 9/2004 | Berreklouw ................... 623/2.1 |
| 7,094,246 B2 | * | 8/2006 | Anderson et al. ............. 606/148 |
| 7,220,238 B2 | * | 5/2007 | Lynch et al. ....................... 604/8 |
| 8,231,671 B2 | | 7/2012 | Kim |
| 2002/0013571 A1 | | 1/2002 | Goldfarb |
| 2002/0183838 A1 | | 12/2002 | Liddicoat et al. |
| 2003/0040793 A1 | * | 2/2003 | Marquez ...................... 623/2.36 |
| 2004/0098116 A1 | | 5/2004 | Callas |
| 2004/0138525 A1 | * | 7/2004 | Saadat et al. .................. 600/104 |
| 2005/0043784 A1 | * | 2/2005 | Yampolsky et al. .......... 623/1.35 |
| 2005/0137451 A1 | | 6/2005 | Gordon |
| 2007/0010829 A1 | * | 1/2007 | Nobles et al. ................. 606/148 |
| 2007/0088432 A1 | * | 4/2007 | Solovay et al. ................ 623/4.1 |
| 2008/0228165 A1 | * | 9/2008 | Spence et al. ................. 604/510 |
| 2008/0228201 A1 | | 9/2008 | Zarbatany |
| 2008/0245371 A1 | * | 10/2008 | Gruber .......................... 128/831 |
| 2008/0294175 A1 | * | 11/2008 | Bardsley et al. .............. 606/113 |
| 2008/0306465 A1 | * | 12/2008 | Bailey et al. .................. 604/500 |
| 2009/0112234 A1 | * | 4/2009 | Crainich et al. .............. 606/144 |
| 2011/0054597 A1 | | 3/2011 | Kim |
| 2012/0029629 A1 | | 2/2012 | Kim |
| 2012/0179246 A1 | | 7/2012 | Kim |

\* cited by examiner (a)

(b)

(a)

(b)

MITRAL CERCLAGE ANNULOPLASTY APPARATUS

CROSS-REFERENCE TO RELATED APPLICATIONS

This is a divisional application for U.S. Ser. No. 12/631,803, filed on Dec. 4, 2009 now U.S. Pat. No. 8,231,671, which claims the benefit of U.S. Provisional Application No. 61/239,828 filed on Sep. 4, 2009 and claims foreign priority benefit of Korean Patent Application No. 10-2009-0080708 filed on Aug. 28, 2009 which is incorporated herein in its entirety.

FIELD OF THE DISCLOSURE

The present disclosure relates to annuloplasty devices and techniques in which the coronary sinus and the tricuspid valve are protected from erosion using a tissue protective device while maintaining appropriate tension by using a knot delivery device.

BACKGROUND OF THE INVENTION

The heart is the center of human circulatory system that pumps blood through our body. It is a muscle that pumps the blood only in one direction. In order for the heart to effectively keep this unidirectional flow of blood, it must have properly functional valves that prevent back flow through its system, or regurgitation. The heart is divided into four chambers, right and left atria, and right and left ventricles. The four chambers are connected to the aorta, the inferior and superior vena cavas, the pulmonary artery, and the pulmonary veins.

The mitral valve ("MV") separates the left atrium from the left ventricle while the tricuspid valve (TV) separates the right atrium from the right ventricle. The aortic valve ("AV") is located between the left ventricle and the aorta while the pulmonary valve ("PV") is located between the right ventricle and the pulmonary artery.

Generally, valves should open and close completely with every heart beat or contraction. Incomplete opening and closing of the valves cause improper flow of blood. Valvular diseases are divided into two categories, regurgitation and stenosis. Regurgitation is a failure of valve to close completely and stenosis is a failure of valve to open completely.

Mitral valve regurgitation ("MVR") is a common cardiac valve disorder that is caused by an incomplete closure of the MV. The MV is located between the left atrium and the left ventricle. Over time, MVR burdens the heart and worsens its ability to pump blood properly. Such stress on the heart will ultimately lead to a heart failure.

Traditional treatment of a worsening MVR requires an open heart surgery with sternotomy or thoracotomy with cardiac arrest and cardiopulmonary bypass. Once the chest is open and access to the heart is gained, the MV is either repaired or replaced using an artificial valve.

Although very effective, this open-heart procedure is a high risk surgery accompanied by substantial morbidity and prolonged convalescence. The mortality due to the surgery itself can be as high as 5%. As a result, the procedure often is not offered to patients who are insufficiently symptomatic to justify the surgical risk and morbidity, or to patients with substantial co-morbidity. It is reserved only for those with severe symptomatic MVR.

This high morbidity rate of an open heart surgery has motivated further research to develop a safer and less risky alternatives to repair an MVR. Much of the research involves the use of cardiac catheterization.

Recently, this inventor presented a thesis regarding "mitral valve cerclage coronary sinus annuloplasty (MVA)" showing outstanding result of an MVR treatment through applying circular pressure around the mitral annulus. This thesis has been filed through PCT as an international patent application and published with its publication number WO2008/060553, which is incorporated herein in its entirety.

The aforementioned thesis and published patent application disclosed the mitral cerclage coronary annuloplasty ("MVA") procedure. Briefly explained, a catheter is placed at the coronary sinus after accessing the right atrium through the jugular vein, and then a cerclage suture is passed through the proximal septal vein.

This cerclage suture can easily pass through the right ventricular outflow tract ("RVOT"), and this inventor defines this technique as "the simple mitral cerclage annuloplasty." Then the cerclage suture can be easily pulled into the right atrium thus placing the cerclage suture circumferentially around the mitral annulus.

Once positioned, tension is applied to the cerclage suture and tightens the mitral valve. This brings together the two leaflets of the MV, so that they are approximated and reduce the size of its incomplete closure. This theory can obtain a very similar result when compared to the results of a conventional surgery that directly tightens the mitral annulus, and show immediate reduction of an MVR.

However, there are several technical problems to be solved. First, there is a need to have a tension locking device to be able to apply proper tension to the cerclage suture and maintain the tension.

According to the aforementioned research result, approximately 400-1200 g tension is needed to have a good treatment result. In addition, individualized tension must be applied constantly until the point where the mitral regurgitation is reduced, then, the suture needs to be fixed at that point, so that the same tension is maintained. Further, this tension must be sustained regardless of its constant resistance from every beat of each heart contraction.

Since this tension is maintained with a very fine cerclage suture (i.e., 0.014 nylon cerclage used in the researches), it can cause damages on the neighboring cardiac tissues where the suture contacts and exerts its pressure. Especially, since the cerclage wraps around the tricuspid valve (TV), it could affect the function of the TV and damage the valve itself and its appendages. This invention is intended to provide viable solutions to overcome these problems.

SUMMARY OF THE INVENTION

The objective of this invention is to overcome the shortcomings of a conventional MVA. In addition, this invention provides techniques and devices designed for the MVA to deliver proper, safe, and effective tension on the cerclage suture.

The other objective is to provide a protective device for tissues, and prevent damage from direct tissue to cerclage suture contact. In addition, it provides a knot delivery device ("KDD") which allows easier way of controlling, adjusting and fixing the tension of the cerclage suture, so that it can be customized for each individual patient. It further provides a tension locking function in which the fixed cerclage suture is maintained without becoming loose.

This invention achieves the aforementioned objectives by using an apparatus described here. Generally, the apparatus comprises a tissue protective device and a knot delivery device.

The tissue protective device comprises a first protective tube and a second protective tube. The first tube and the second tube each have a proximal portion and a distal portion. The proximal portions of the two tubes are attached side-by-side longitudinally along at least a portion of the length of the two protective tubes. The distal portions of the two tubes are separated thereafter.

In a first embodiment, KDD comprises a tube having a proximal end, a hole, and a distal end, wherein a loose knot is looped around the distal end through the hole and wherein a tight knot is formed when the distal end of the tube is cut open.

In a second embodiment, KDD comprises an inner tube and an outer tube. The inner tube and the outer tube each have a proximal end and a distal end. The inner tube is insertable and rotatable inside the outer tube. The distal ends of each tubes have an opening. The opening of the inner tube is further divided into a small opening and a large opening.

When the tubes are in a closed position by rotating either the outer tube or the inner tube, a hole is created near the distal end. In addition, when the tubes are in open position by rotating either the outer tube or the inner tube, the hole joins the opening of the outer tube, and lengthens.

BRIEF DESCRIPTION OF THE DRAWINGS

FIG. 4(a) shows KDD whose distal end has a hole in a closed position where a loose knot is looped around the distal end through the hole.

FIG. 4(b) shows the distal end of the tube is cut off in open position where a tight knot is formed.

FIG. 5(a) shows a step of making a loose knot around the distal end of KDD through the hole using a cerclage suture.

FIG. 5(b) shows a step of tension adjustment where the suture can be pulled or released until the mitral regurgitation stops.

FIG. 5(c) shows a step of cutting off (or opening) the hole, so that the loose knot is ready to form a tight knot.

FIG. 5(d) shows a step of tightening the knot while maintaining the right amount of tension on the cerclage suture.

FIG. 5(e) shows a step of cutting off the cerclage suture.

FIG. 5(f) shows the final step of the cerclage procedure.

FIG. 6(a) shows KDD in a closed position where a hole is created near the distal end of KDD by rotating either the outer tube or the inner tube, so that a loose knot is formed around the distal end of KDD through the hole using a cerclage suture.

FIG. 6(b) shows KDD in an open position where an opening is created near the distal end of KDD by rotating either the outer tube or the inner tube, so that a loose knot is ready to form a tight knot without cutting in a step shown in FIG. 4(a).

DETAILED DESCRIPTION OF THE INVENTION

The detailed disclosure of the mitral valve cerclage coronary sinus annuloplasty ("MVA") comprising of a coronary sinus and tricuspid valve protective device ("CSTVPD"), and a knot delivery device ("KDD") will be discussed.

Figure 1:
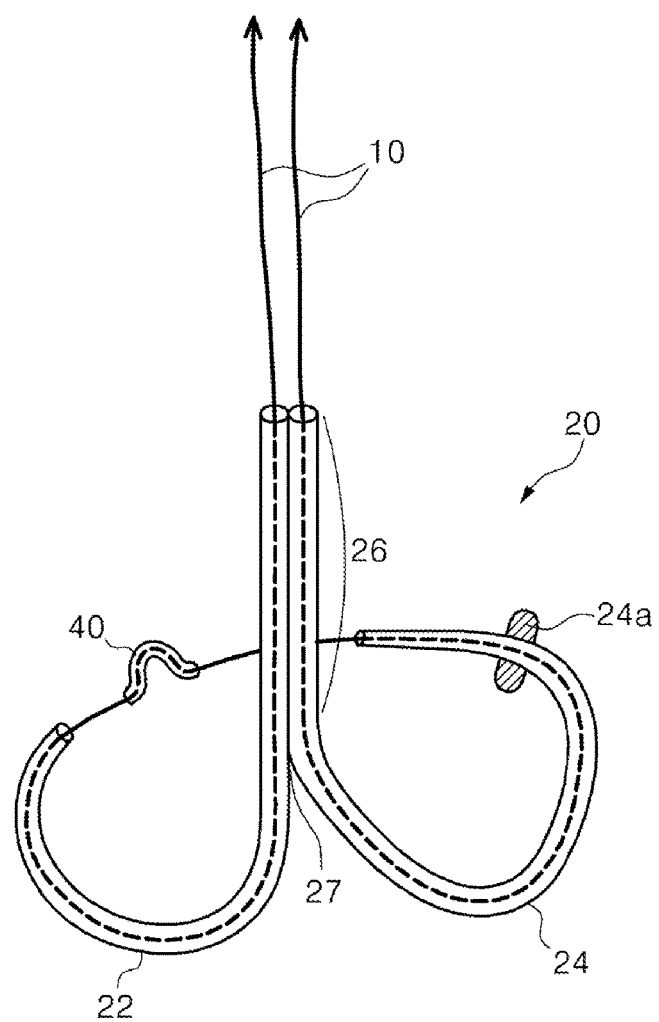
FIG. 1 shows a protection device in a particular embodiment, comprising a coronary sinus tube, a tricuspid valve tube, a hinge portion, a stem portion, a ring-shape stopper, a coronary protection device, and a cerclage suture.
Figure 2:
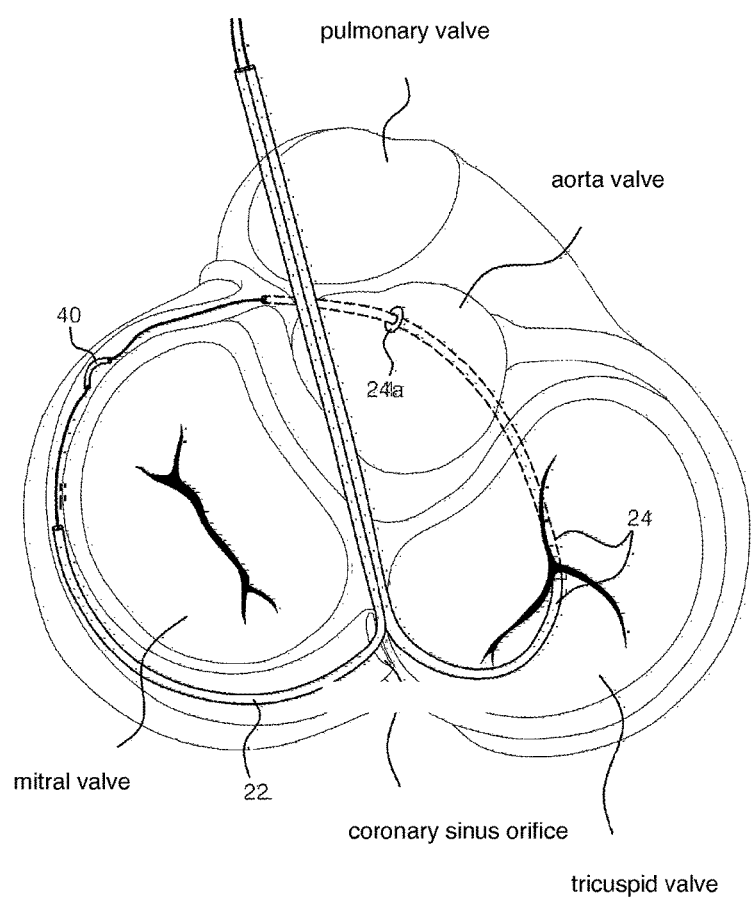
FIG. 2 is a schematic view of a cross-sectional top view of the heart, taken at the level of the atrioventricular valves, showing the protective device in place.
Figure 3:
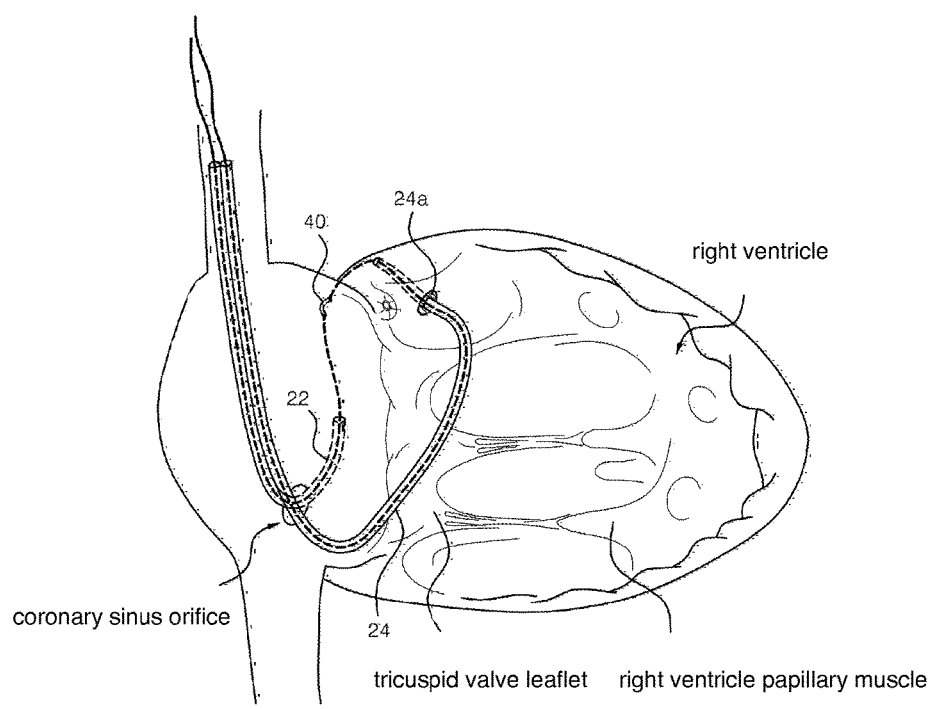
FIG. 3 is a front view of the heart with portions of the myocardial wall removed to show the protective device in place.

According to FIGS. 1-3, CSTVPD 20 includes a coronary sinus tube 22 ("CS tube"), a tricuspid valve tube 24 ("TV tube"), and a stem portion 26. CS tube 22 encircles the coronary sinus ("CS"), and TV tube 24 encircles the tricuspid valve ("TV"). Then, extensions of CS tube 22 and TV tube 24 meet and run together to form the stem portion 26.

Generally, conventional MVA techniques cause tissue damage (erosion) to the CS, the TV, and the intraventricular septum ("IVS") from direct cerclage suture to tissue contact. These critical structures can be protected from damage by using CSTVPD 20 around the cerclage suture.

A part of the CS is protected by a coronary protective device 40 ("CPD") introduced in the previous MVA thesis. Thus, only the remainder of the CS will need to be protected.

CSTVPD 20 has two separated tubes, CS tube 22 and TV tube 24 which extend and form the stem portion 26. The thickness of the tubes are approximately 4 Fr diagnostic catheter made of a flexible rubber or a plastic like material. CSTVPD 20 is named because it protects both the CS and the TV.

In a MVA procedure, first, a cerclage suture is fed through out CSTVPD 20 starting at the CS extension of the stem portion 26, CS tube 22, CPD 40, TV tube 24, and back out through the TV extension of the stem portion 26, or in reverse direction. Then, the suture-inserted CSTVPD 20 is pushed into the body through a catheter and positioned within the heart.

Then, CS tube 22 is positioned to wrap around the CS, and the TV tube 24 is positioned to wrap around the TV leaflets. Since the cerclage suture 10 is inside the tubes and not in direct contact with the surrounding tissue, the cardiac tissues around the CS, the TV and the IVS are protected from damage from the cerclage suture 10.

CS tube 22 is a part of a coronary sinus protection device. CS tube 22 starts at the orifice of the CS to the beginning of the CPD 40. Anatomically, this length varies from patient to patient. Thus, before the procedure, an appropriate length can be determined using an estimation from a CT or other imaging methods. CS tube 22 should be made of a soft and flexible catheter like material, so that its effect on compression of the CS is minimized.

TV tube 24 has tapering shape towards its end. Starting from the stopper 24a, the TV tube 24 passes through the muscle of the IVS. Therefore, to ease the passing through the IVS muscle, TV tube 24 should taper from the stopper 24a to the end.

In addition, TV tube 24 has a ring-shaped stopper 24a (RVOT exit stopper 24a) positioned about mid length of TV tube 24 to prevent further advancement of TV tube 24 into the heart muscle.

Again, the length of TV tube 24 shall vary from patient to patient. The length shall be determined based on the estimation from prior imaging studies of an individual patient.

Preferably, the length of the TV tube 24 from the hinge portion 27 to the stopper 24a shall be derived by actual endocardial surface length from the 'RVOT exit' to the 'CS opening.' It should be longer than actual endocardial surface length to be redundant. This distance from the stopper 24a to the tapered end of the TV tube 24 shall be determined by preintervention imaging analysis. Obviously, the location of the stopper 24a can vary as needed, and the length from the hinge portion 27 to the stopper 24a can also vary depending on the need.

The hinge portion 27, where the CS tube 22 and the TV tube 24 meet, shall be placed at or near the orifice of the CS. The TV tube 24 will be fixed to the heart at the hinge portion 27 and at the stopper 24a. Then, the hinge portion 27 to the stopper 24a portion of the TV tube 24 can be suspended freely in a reverse "C" shape without being directly attached to the tissue. Such technique can reduce the TV tissue damage resulting from direct contact of the cerclage suture, and it also reduces the restriction of cerclage on movement of the TV leaflets.

The TV tube 24 shall be rigid enough to resist being bent as tension is applied onto the cerclage suture. On the other hand, it shall be flexible enough to bend in the reverse "C" shape.

The stem portion 26 plays two roles. First, it stabilizes the CS tube 22 and the TV tube 24, so that their position is well maintained. Second, since the hinge portion 27 rests on the orifice of the CS, it prevents further advancement of the CSTVPD 20 into the CS. The stem portion 26 (where the CS tube 22 and the TV tube 24 are adjoined) should be made of a semi-rigid catheter like material.

Figure 4:
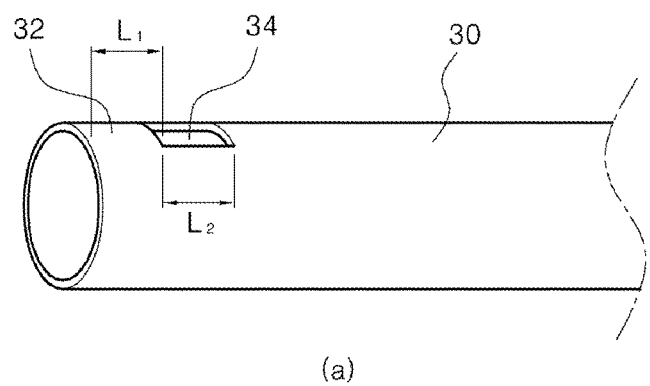
FIG. 4 is a set of drawings showing a knot delivery device ("KDD") in a first embodiment using one tube configuration.
Figure 4:
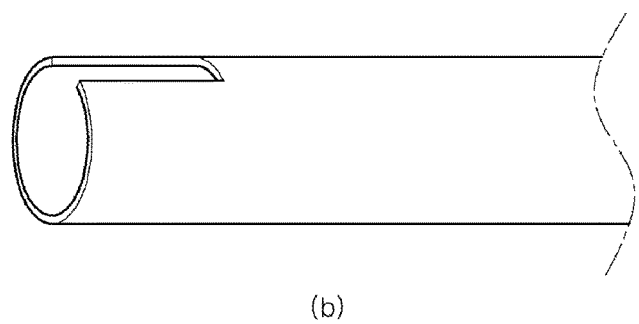

FIG. 4 shows a knot delivery device 30 ("KDD") in a first embodiment. KDD 30 is designed to transfer the cerclage suture 10 looped and ready to be knotted to the upper portion of the CSTVPD 20 while maintaining a constant tension on the cerclage suture.

Once positioned and appropriate tension is verified, the KDD 30 will release the loop and knot the suture in place, thus, ensuring the knot is positioned in the right place with an appropriate amount of tension.

One of the most crucial component of an MVA procedure is having a device that can deliver and maintain necessary tension enough to apply compression on the mitral annulus. That device should be (1) easy to operate, (2) easy to manipulate cerclage suture tension depending on an individual patient variance, and (3) easy to readjust and fix tension. Then once cerclage suture is fixed, (4) the suture should not become loose and maintain its constant tension well after the procedure.

FIG. 4 is a set of drawings showing the KDD 30 in the first embodiment using one tube configuration. FIG. 4(a) shows the KDD 30 whose distal end has a hole in a closed position where a loose knot is looped around the distal end through the hole. FIG. 4(a) shows the distal end of the tube is cut off in a closed position where a tight knot is formed. FIG. 4(b) shows the distal end of the tube is cut off in an open position where a tight knot is formed.

The KDD 30 is a catheter where a portion 32 of the distal end of the KDD 30 can be in a closed position next to a hole 34 where a loose knot is looped around the portion 32 through the hole. The portion 32 is cut off in an opened position where a loose knot becomes a tight knot.

The KDD 30 should be made of a sturdy material often used in diagnostic catheters. It can be made of rubber or plastic like material strong enough to be pushed inside the body from outside.

As shown in FIG. 4(a) with portion 32 in a closed position, a cerclage suture 10 is made into a loop ready to be knotted at the distal end of the KDD 30. Then, the KDD 30 with the loosely knotted cerclage suture 10 is advanced inside the body and positioned appropriately. Then tension is applied and adjusted. When position and tension is verified, the portion 32 is cut off as in FIG. 4(b), fixing the knot in place while maintaining the same amount of tension on the cerclage suture.

Figure 5:
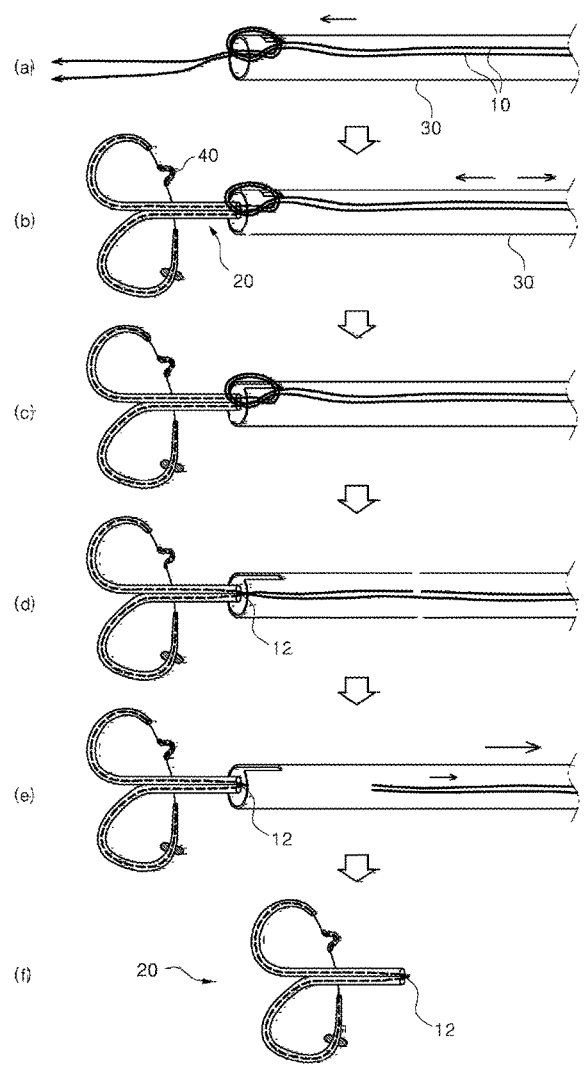
FIG. 5 is a set of drawings showing detailed steps of KDD operation in a first embodiment.

FIG. 5 shows detailed steps of The KDD 30 operation. FIG. 5 shows each steps of KDD 30 during a MVA procedure.

In summary, FIG. 5 is a set of drawings showing detailed steps of KDD 30 operation in a the first embodiment. FIG. 5(a) shows a step of making a loose knot around the distal end of the KDD 30 through the hole 34 using the cerclage suture 10. FIG. 5(b) shows a step of tension adjustment where the suture 10 can be pulled or released until the mitral regurgitation stops.

FIG. 5(c) shows a step of cutting off (or opening) hole 34, so that the loose knot is ready to form a tight knot 12. FIG. 5(d) shows a step of tightening the knot while maintaining the right amount of tension on the cerclage suture 10. FIG. 5(e) shows a step of cutting off the cerclage suture 10. Lastly, FIG. 5(f) shows the final step of the cerclage procedure.

According to FIG. 5, first, two strands of the cerclage suture 10 are inserted through the hole 34 at the distal end of KDD 30. Second, two strands are looped and made ready to form a knot 12. Third, the two strands are passed through the body of KDD 30. Fourth, KDD 30 is advanced into the heart and positioned at the end of the stem portion 26 of CSTVPD 20. Hence, KDD 30 delivers the cerclage suture knot to CSTVPD 20 while keeping the knot 12 from tightening until it is ready to be fixed.

Then, appropriate amount of tension is applied to the cerclage suture 10 and adjusted until the mitral regurgitation ceases. In other words, the tension on the cerclage suture 10 is adjusted by pulling or releasing the strands until the mitral regurgitation stops.

Once the right amount of tension is achieved, a portion 32 of the KDD 30 is cut off from the KDD 30. The portion 32 of the KDD 30 can be cut with a cutter or as explained below in FIG. 4, various methods can be utilized.

When the portion 32 is cut off from the KDD 30, the loop tightens into a knot 12 while maintaining the right amount of tension on the cerclage suture as shown in FIG. 5(d), so that the end of the cerclage suture is knotted at the distal end of the stem portion 26 of CVTVPD 20. Once the knot 12 is placed and tightened at the end of the stem portion 26, the stem portion 26 can now hold the two strands aligned and in place. This also enables the knot 12 from becoming loose even under a significant amount of tension from the constant beat to beat contraction of the heart.

At this stage, the cerclage suture 10 is cut at a certain distance from the knot 12 with a cutter as shown in FIG. 5(e). Then, the remainder of the cerclage suture 10 and the KDD 30 is retracted from the body as shown in FIG. 5(f). Thus, upon completion of CSTVPD 20 procedure, CS tube 22 and TV tube 24 protects the surrounding tissue from cerclage suture 10 while maintaining constant tension on the cerclage suture 10.

Figure 6:
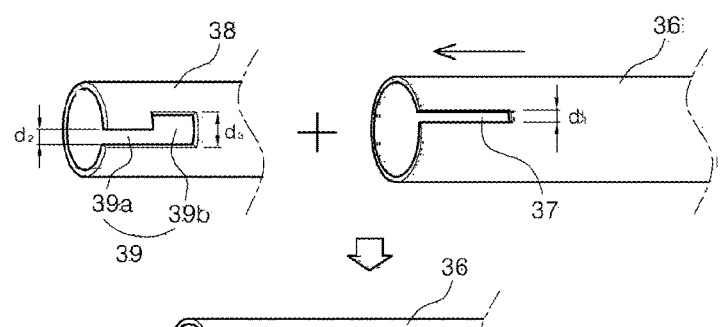
FIG. 6 is a set of drawings showing a detailed operation of KDD in a second embodiment using an inner tube and an outer tube.
Figure 6:
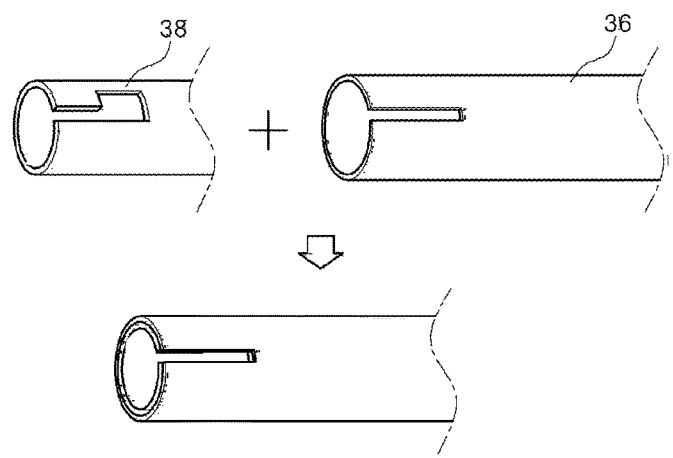

FIG. 6 is a set of drawings showing detailed operation of the KDD 30 in a second embodiment using an inner tube 38 and an outer tube 36. The inner tube 38 and the outer tube 36 each have a proximal end and a distal end. The inner tube 38 is insertable and rotatable inside the outer tube 36.

The distal end of the inner tube 38 has an opening 39. The opening 39 is further divided into a small opening 39a and a larger opening 39b. The distal end of the outer tube 36 has an opening 37.

When the tubes 38, 36 are in a closed position by rotating either outer tube 36 or inner tube 38, a hole 34 is created near the distal end. Likewise, when the tubes 38, 36 in an opened position by rotating either the outer tube 36 or the inner tube 38, the hole 34 joins the opening 37 of the outer tube 36 and lengthens. The outer tube 36 and the inner tube 38 are made of a basic catheter type of material.

FIG. 6(a) shows the KDD 30 in a closed position where a hole 34 is created near the distal ends of the KDD 30 by rotating either the outer tube 36 or the inner tube 38, so that a loose knot is formed around the distal ends of the KDD 30 through the hole 34 using the cerclage suture 10.

FIG. 6(b) shows the KDD 30 in an open position where an opening is created near the distal ends of the KDD 30 by rotating either the outer tube 36 or the inner tube 38, so that a loose knot is ready to form a tight knot 12 without a cutting step shown in FIG. 4(b).

In a preferred embodiment, the inner tube 38 has the small opening 39a whose length is L1 and whose diameter is d2, and the large opening 39b whose length is L2 and whose diameter is d3, wherein the opening 37 in outer tube 36 has a length less than or equal to the sum of L1 and L2- and diameter d1, wherein d3 is larger or equal to the sum of d1 and d2.

While the invention has been described in terms of specific embodiments, it is apparent that other forms could be adopted by one skilled in the art. Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention.

The invention claimed is:

1. A set of devices for mitral valve annuloplasty, comprising: a tissue protective device, the tissue protective device having a cerclage suture disposed within a first protective tube and a second protective tube, the first protective tube and the second protective tube each having a proximal portion and a distal portion, the proximal portions of the two protective tubes being attached side-by-side longitudinally along at least a portion of the length of the two protective tubes, the distal portions of the two protective tubes being separated thereafter, and a knot delivery device comprising an inner tube and an outer tube having a proximal end and a distal end, wherein the inner tube is insertable and rotatable inside the outer tube, wherein the distal ends of each the inner and outer tubes have an opening, wherein the opening of the inner tube is further divided into a small opening and a large opening, wherein when the inner and outer tubes are in a closed position, by rotating either the outer tube or the inner tube, a hole is created near the distal end of the knot delivery device, such that the hole forms an overall opening of the knot delivery device, and wherein when the inner and outer tubes are in an open position, by rotating either the outer tube or the inner tube, the hole is part of the overall opening in the knot delivery device with the opening of the outer tube and the length of the overall opening in the knot delivery device increases to that of the opening of the inner tube, wherein the end of the cerclage suture pass through the hole and the large opening of the inner tube.

2. The set of devices according to claim 1, wherein the tissue protective device further comprises a ring-shaped stopper being positioned on the distal portion of the second protective tube to prevent further advancement of the second protective tube into heart muscle.

3. The set of devices according to claim 1, wherein the distal portion of the second protective tube has a tapering shape towards its end.

4. The set of devices according to claim 1, wherein the first protective tube is made of flexible rubber or plastic material and has a diameter approximately equivalent to a 4 Fr diagnostic catheter.

5. The set of devices according to claim 1, wherein the distal portion of the first protective tube has an arched configuration so that the distal portion can be positioned to encircle a coronary sinus.

6. The set of devices according to claim 1, wherein the second protective tube is made of flexible rubber or plastic material and has a diameter approximately equivalent to a 4 Fr diagnostic catheter.

7. The set of devices according to claim 1, wherein the distal portion of the second protective tube is flexible enough to form an arch that encircles a tricuspid valve.

8. The set of devices according to claim 1, wherein the distal portion of the second protective tube is rigid enough to resist being bent inward as tension is applied.

9. The set of devices according to claim 1, wherein the inner tube has the small opening whose length is L1 and diameter is d2, and the large opening whose length is L2 and diameter is d3, wherein the outer tube has an opening with a length less than or equal to the sum of L1 and L2, and diameter d1, and wherein d3 is larger or equal to the sum of d1 and d2.

10. A device for reducing mitral valve regurgitation, comprising:
an elongated body comprising a proximal portion and a distal portion, the distal portion separating into a first arm and a second arm to create a hinge portion, each of the proximal and the distal portions dimensioned to reside completely within the vascular system wherein a cerclage suture disposed within the elongated body, the first arm, and the second arm for applying tension,
the first arm configured to wrap around a mitral valve annulus, the first arm adapted to be delivered into a coronary sinus, the first arm configured to be positioned within the coronary sinus adjacent the mitral valve annulus, the first arm configured to have a first arched configuration starting at the hinge portion such that the first arm encircles the coronary sinus as the tension is applied,
the second arm configured to wrap around a tricuspid leaflet, the second arm having a stopping element disposed on a distal portion of the second arm, the second arm configured to have a second arched configuration between the hinge portion and the stopping element such that the second arm resists being bent inward as the tension is applied,
the hinge portion configured to be so positioned at or near a coronary sinus orifice such that the first arm is prevented from further advancement, the hinge portion configured to stabilize the first arm and the second arm with respect to a heart tissue, the hinge portion configured in such a way that the second arm forms an arch from the hinge portion to the stopping element such that the arch is suspended freely as the tension is applied.

11. The device according to claim 10, wherein the distal portion of the second arm is tapered.

12. The device according to claim 10, the first arm and the second arm are made of a flexible material.

13. The device according to claim 10, wherein the first arm and the second arm have a diameter approximately equivalent to a 4 Fr diagnostic catheter.

14. A device for reducing mitral valve regurgitation, comprising:
an elongated body comprising a proximal portion and a distal portion, the distal portion separating into a first arm and a second arm to create a hinge portion, each of the proximal and the distal portions dimensioned to reside completely within the vascular system wherein a cerclage suture disposed within the elongated body, the first arm, and the second arm for applying tension,
the first arm having means for wrapping around a mitral valve annulus,
the second arm having means for wrapping around a tricuspid leaflet, the second arm having a stopping element disposed on a distal portion of the second arm,
the first arm configured to be positioned within a coronary sinus adjacent the mitral valve annulus,
the hinge portion configured to be so positioned at or near a coronary sinus orifice such that the first arm is prevented from further advancement, the second arm having a stopper element thereon.

15. The device according to claim 14, wherein the distal portion of the second arm is tapered.

16. The device according to claim 14, the first arm and the second arm are made of a flexible material.

17. The device according to claim 14, wherein the first arm and the second arm have a diameter approximately equivalent to a 4 Fr diagnostic catheter.

18. The device according to claim 14, wherein the hinge portion is adapted to stabilize the first and the second arms with respect to a heart tissue.

19. The device according to claim 14, wherein a distal portion of the first arm has an arched configuration so that the distal portion is configured to be positioned to encircle the coronary sinus.

20. The device according to claim 14, wherein the distal portion of the second arm is rigid enough to resist being bent inward as tension is applied.

21. The device according to claim 14, wherein a portion of the second arm from the hinge portion to the stopper element forms an arch so that the arch is suspended freely.

* * * * *